(12) United States Patent
DeBusschere et al.

(10) Patent No.: US 10,080,528 B2
(45) Date of Patent: Sep. 25, 2018

(54) OPTICAL CENTRAL VENOUS PRESSURE MEASUREMENT

(71) Applicant: Google, Inc., Mountain View, CA (US)

(72) Inventors: Brian Derek DeBusschere, Los Gatos, CA (US); James Moad Reid, Mountain View, CA (US); Jeffrey L. Rogers, San Carlos, CA (US)

(73) Assignee: Google LLC, Mountain View, CA (US)

( * ) Notice: Subject to any disclaimer, the term of this patent is extended or adjusted under 35 U.S.C. 154(b) by 97 days.

(21) Appl. No.: 14/715,793

(22) Filed: May 19, 2015

(65) Prior Publication Data
US 2018/0177464 A1    Jun. 28, 2018

(51) Int. Cl.
*A61B 5/00* (2006.01)
*A61B 5/021* (2006.01)
(Continued)

(52) U.S. Cl.
CPC .......... *A61B 5/7278* (2013.01); *A61B 5/0013* (2013.01); *A61B 5/0075* (2013.01);
(Continued)

(58) Field of Classification Search
CPC ... A61B 5/0013; A61B 5/0064; A61B 5/0077; A61B 5/02; A61B 5/021; A61B 5/02116;
(Continued)

(56) References Cited

U.S. PATENT DOCUMENTS

| | | |
|---|---|---|
| 5,121,124 A | 6/1992 | Spivey et al. |
| 5,410,471 A | 4/1995 | Alyfuku et al. |

(Continued)

FOREIGN PATENT DOCUMENTS

| | | |
|---|---|---|
| CN | 102660988 | 3/2014 |
| EP | 2417908 | 2/2012 |

(Continued)

OTHER PUBLICATIONS

"Final Office Action", U.S. Appl. No. 14/599,954, dated Aug. 10, 2016, 23 pages.

(Continued)

*Primary Examiner* — Scott Getzow
(74) *Attorney, Agent, or Firm* — Colby Nipper

(57) ABSTRACT

This document describes optical central venous pressure measurement. To determine the central venous pressure (CVP) of a person optically, video of a right side of the person's neck is captured. By way of example, a medical professional records a video of the right side of the person's neck using a smartphone. The right side of the person's neck is captured because it is where the person's external and internal jugular veins are located and pulsatile motions that are usable to measure CVP occur in those veins. The video is then processed according to video motion amplification techniques to generate a reconstructed video of the right side of the person's neck. In the reconstructed video, the pulsatile motion of the person's venous system that occurs at the right side of their neck is visually amplified. Using the reconstructed video, measurements are made of a distance between a peak of the visually-amplified pulsatile motion and an anatomical feature of the person. The measured distance between the peak of the visually-amplified pulsatile motion and the anatomical feature is used to determine CVP of the person. These techniques enable CVP to be determined without relying on estimates made by medical professionals.

20 Claims, 6 Drawing Sheets

(51) Int. Cl.
  *A61B 5/107* (2006.01)
  *A61B 5/0205* (2006.01)
  *A61B 5/024* (2006.01)
  *A61B 5/08* (2006.01)

(52) U.S. Cl.
  CPC .......... *A61B 5/0077* (2013.01); *A61B 5/0205* (2013.01); *A61B 5/02125* (2013.01); *A61B 5/1072* (2013.01); *A61B 5/1079* (2013.01); *A61B 5/6898* (2013.01); *A61B 5/725* (2013.01); *A61B 5/7246* (2013.01); *A61B 5/7275* (2013.01); *A61B 5/7285* (2013.01); *A61B 5/742* (2013.01); *A61B 5/7475* (2013.01); *A61B 5/02416* (2013.01); *A61B 5/0816* (2013.01); *A61B 2560/0475* (2013.01); *A61B 2562/0233* (2013.01); *A61B 2576/00* (2013.01)

(58) Field of Classification Search
  CPC .......... A61B 5/026; A61B 5/029; A61B 5/103; A61B 5/1072
  See application file for complete search history.

(56) References Cited

U.S. PATENT DOCUMENTS

| | | | |
|---|---|---|---|
| 5,798,798 | A | 8/1998 | Rector et al. |
| 6,254,544 | B1 | 7/2001 | Hayashi |
| 6,313,825 | B1 | 11/2001 | Gilbert |
| 6,386,757 | B1 | 5/2002 | Konno |
| 6,513,970 | B1 | 2/2003 | Tabata et al. |
| 6,524,239 | B1 | 2/2003 | Reed et al. |
| 6,616,613 | B1 | 9/2003 | Goodman |
| 7,194,371 | B1 | 3/2007 | McBride et al. |
| 7,317,416 | B2 | 1/2008 | Flom et al. |
| 7,421,061 | B2 | 9/2008 | Boese et al. |
| 7,647,093 | B2 | 1/2010 | Bojovic et al. |
| 7,677,729 | B2 | 3/2010 | Vilser et al. |
| 7,691,067 | B2 | 4/2010 | Westbrook et al. |
| 7,698,154 | B2 | 4/2010 | Marchosky |
| 8,062,220 | B2 | 11/2011 | Kurtz et al. |
| 8,179,604 | B1 | 5/2012 | Prada Gomez et al. |
| 8,193,929 | B1 | 6/2012 | Siu et al. |
| 8,289,185 | B2 | 10/2012 | Alonso |
| 8,301,232 | B2 | 10/2012 | Albert et al. |
| 8,475,367 | B1 | 7/2013 | Yuen et al. |
| 8,509,882 | B2 | 8/2013 | Albert et al. |
| 8,560,972 | B2 | 10/2013 | Wilson |
| 8,562,526 | B2 | 10/2013 | Heneghan et al. |
| 8,655,004 | B2 | 2/2014 | Prest et al. |
| 8,700,137 | B2 | 4/2014 | Albert |
| 8,758,020 | B2 | 6/2014 | Burdea et al. |
| 8,764,651 | B2 | 7/2014 | Tran |
| 8,790,257 | B2 | 7/2014 | Libbus et al. |
| 8,819,812 | B1 | 8/2014 | Weber et al. |
| 9,230,160 | B1 | 1/2016 | Kanter |
| 9,508,141 | B2 * | 11/2016 | Khachaturian ........ A61B 5/742 |
| 9,594,443 | B2 | 3/2017 | VanBlon et al. |
| 9,600,080 | B2 | 3/2017 | Poupyrev |
| 9,778,749 | B2 | 10/2017 | Poupyrev |
| 9,811,164 | B2 | 11/2017 | Poupyrev |
| 9,848,780 | B1 | 12/2017 | Debusschere et al. |
| 9,921,660 | B2 | 3/2018 | Poupyrev |
| 10,016,162 | B1 | 7/2018 | Rogers et al. |
| 2003/0093000 | A1 | 5/2003 | Nishio et al. |
| 2003/0122677 | A1 | 7/2003 | Kail |
| 2004/0102693 | A1 | 5/2004 | Debusschere et al. |
| 2004/0249250 | A1 | 12/2004 | McGee et al. |
| 2005/0148876 | A1 | 7/2005 | Endoh et al. |
| 2006/0040739 | A1 | 2/2006 | Wells |
| 2007/0118043 | A1 | 5/2007 | Oliver et al. |
| 2007/0161921 | A1 | 7/2007 | Rausch |
| 2007/0176821 | A1 | 8/2007 | Flom et al. |
| 2007/0197878 | A1 | 8/2007 | Shklarski |
| 2008/0001735 | A1 | 1/2008 | Tran |
| 2008/0015422 | A1 | 1/2008 | Wessel |
| 2008/0039731 | A1 | 2/2008 | McCombie et al. |
| 2008/0065291 | A1 | 3/2008 | Breed |
| 2008/0168396 | A1 | 7/2008 | Matas et al. |
| 2008/0194975 | A1 | 8/2008 | MacQuarrie et al. |
| 2008/0211766 | A1 | 9/2008 | Westerman et al. |
| 2008/0316085 | A1 | 12/2008 | Rofougaran et al. |
| 2008/0320419 | A1 | 12/2008 | Matas et al. |
| 2009/0018408 | A1 | 1/2009 | Ouchi et al. |
| 2009/0058820 | A1 | 3/2009 | Hinckley |
| 2009/0113298 | A1 | 4/2009 | Jung et al. |
| 2009/0115617 | A1 | 5/2009 | Sano et al. |
| 2009/0177068 | A1 | 7/2009 | Stivoric et al. |
| 2009/0253585 | A1 | 10/2009 | Diatchenko et al. |
| 2009/0270690 | A1 | 10/2009 | Roos et al. |
| 2009/0295712 | A1 | 12/2009 | Ritzau |
| 2009/0319181 | A1 | 12/2009 | Khosravy et al. |
| 2010/0069730 | A1 | 3/2010 | Bergstrom et al. |
| 2010/0094141 | A1 | 4/2010 | Puswella |
| 2010/0179820 | A1 | 7/2010 | Harrison et al. |
| 2010/0204550 | A1 | 8/2010 | Heneghan et al. |
| 2010/0281438 | A1 | 11/2010 | Latta et al. |
| 2010/0292549 | A1 | 11/2010 | Schuler |
| 2010/0306713 | A1 | 12/2010 | Geisner et al. |
| 2010/0324384 | A1 | 12/2010 | Moon et al. |
| 2011/0003664 | A1 | 1/2011 | Richard |
| 2011/0010014 | A1 | 1/2011 | Oexman et al. |
| 2011/0029038 | A1 | 2/2011 | Hyde et al. |
| 2011/0093820 | A1 | 4/2011 | Zhang et al. |
| 2011/0118564 | A1 | 5/2011 | Sankai |
| 2011/0181509 | A1 | 7/2011 | Rautiainen et al. |
| 2011/0197263 | A1 | 8/2011 | Stinson, III |
| 2011/0202404 | A1 | 8/2011 | van der Riet |
| 2011/0213218 | A1 | 9/2011 | Weiner et al. |
| 2011/0221666 | A1 | 9/2011 | Newton et al. |
| 2011/0234492 | A1 | 9/2011 | Ajmera et al. |
| 2011/0239118 | A1 | 9/2011 | Yamaoka et al. |
| 2011/0245688 | A1 | 10/2011 | Arora et al. |
| 2011/0307842 | A1 | 12/2011 | Chiang et al. |
| 2012/0019168 | A1 | 1/2012 | Noda et al. |
| 2012/0029369 | A1 | 2/2012 | Icove et al. |
| 2012/0047468 | A1 | 2/2012 | Santos et al. |
| 2012/0123232 | A1 | 5/2012 | Najarian et al. |
| 2012/0174736 | A1 | 7/2012 | Wang et al. |
| 2012/0220835 | A1 | 8/2012 | Chung |
| 2012/0254810 | A1 | 10/2012 | Heck et al. |
| 2012/0280900 | A1 | 11/2012 | Wang et al. |
| 2012/0310665 | A1 | 12/2012 | Xu et al. |
| 2013/0035563 | A1 | 2/2013 | Angellides |
| 2013/0053653 | A1 | 2/2013 | Cuddihy et al. |
| 2013/0083173 | A1 | 4/2013 | Geisner et al. |
| 2013/0096439 | A1 | 4/2013 | Lee et al. |
| 2013/0132931 | A1 | 5/2013 | Bruns et al. |
| 2013/0150735 | A1 | 6/2013 | Cheng |
| 2013/0195330 | A1 | 8/2013 | Kim et al. |
| 2013/0278499 | A1 | 10/2013 | Anderson |
| 2013/0278501 | A1 | 10/2013 | Bulzacki |
| 2013/0283203 | A1 | 10/2013 | Batraski et al. |
| 2013/0322729 | A1 * | 12/2013 | Mestha ................ A61B 5/02 382/134 |
| 2013/0332438 | A1 | 12/2013 | Li et al. |
| 2013/0345569 | A1 | 12/2013 | Mestha et al. |
| 2014/0005809 | A1 | 1/2014 | Frei et al. |
| 2014/0051941 | A1 | 2/2014 | Messerschmidt |
| 2014/0072190 | A1 | 3/2014 | Wu et al. |
| 2014/0073486 | A1 | 3/2014 | Ahmed et al. |
| 2014/0073969 | A1 | 3/2014 | Zou et al. |
| 2014/0081100 | A1 | 3/2014 | Muhsin et al. |
| 2014/0095480 | A1 | 4/2014 | Marantz et al. |
| 2014/0121540 | A1 | 5/2014 | Raskin |
| 2014/0135631 | A1 | 5/2014 | Brumback et al. |
| 2014/0139616 | A1 | 5/2014 | Pinter et al. |
| 2014/0143678 | A1 | 5/2014 | Mistry et al. |
| 2014/0191939 | A1 | 7/2014 | Penn et al. |
| 2014/0200416 | A1 | 7/2014 | Kashef et al. |
| 2014/0244277 | A1 | 8/2014 | Krishna Rao et al. |
| 2014/0250515 | A1 | 9/2014 | Jakobsson |
| 2014/0253709 | A1 | 9/2014 | Bresch et al. |

(56) References Cited

U.S. PATENT DOCUMENTS

| | | | |
|---|---|---|---|
| 2014/0275854 A1 | 9/2014 | Venkatraman et al. | |
| 2014/0280295 A1 | 9/2014 | Kurochikin et al. | |
| 2014/0297006 A1 | 10/2014 | Sadhu | |
| 2014/0306936 A1 | 10/2014 | Dahl et al. | |
| 2014/0316261 A1 | 10/2014 | Lux et al. | |
| 2014/0357369 A1 | 12/2014 | Callens et al. | |
| 2014/0376788 A1 | 12/2014 | Xu et al. | |
| 2015/0026815 A1 | 1/2015 | Barrett | |
| 2015/0029050 A1 | 1/2015 | Driscoll et al. | |
| 2015/0046183 A1* | 2/2015 | Cireddu | G06F 19/3418 705/3 |
| 2015/0077282 A1 | 3/2015 | Mohamadi | |
| 2015/0085060 A1 | 3/2015 | Fish et al. | |
| 2015/0099941 A1 | 4/2015 | Tran | |
| 2015/0100328 A1 | 4/2015 | Kress et al. | |
| 2015/0112606 A1 | 4/2015 | He et al. | |
| 2015/0277569 A1 | 10/2015 | Sprenger et al. | |
| 2015/0287187 A1 | 10/2015 | Redtel | |
| 2015/0312041 A1 | 10/2015 | Choi | |
| 2015/0346820 A1 | 12/2015 | Poupyrev et al. | |
| 2015/0351703 A1 | 12/2015 | Phillips et al. | |
| 2016/0041617 A1 | 2/2016 | Poupyrev | |
| 2016/0041618 A1 | 2/2016 | Poupyrev | |
| 2016/0054792 A1 | 2/2016 | Poupyrev | |
| 2016/0054803 A1 | 2/2016 | Poupyrev | |
| 2016/0054804 A1 | 2/2016 | Gollakata et al. | |
| 2016/0055201 A1 | 2/2016 | Poupyrev et al. | |
| 2016/0098089 A1 | 4/2016 | Poupyrev | |
| 2016/0100166 A1 | 4/2016 | Dragne et al. | |
| 2016/0106328 A1 | 4/2016 | Mestha et al. | |
| 2016/0206244 A1 | 7/2016 | Rogers | |
| 2016/0213331 A1 | 7/2016 | Gil et al. | |
| 2016/0220152 A1 | 8/2016 | Meriheina et al. | |
| 2016/0287172 A1 | 10/2016 | Morris et al. | |
| 2016/0321428 A1 | 11/2016 | Rogers | |
| 2016/0338599 A1 | 11/2016 | DeBusschere et al. | |
| 2017/0192523 A1 | 7/2017 | Poupyrev | |
| 2018/0000354 A1 | 1/2018 | Debusschere et al. | |
| 2018/0000355 A1 | 1/2018 | Debusschere et al. | |
| 2018/0004301 A1 | 1/2018 | Poupyrev | |
| 2018/0046258 A1 | 2/2018 | Poupyrev | |

FOREIGN PATENT DOCUMENTS

| | | |
|---|---|---|
| FR | 3017722 | 8/2015 |
| JP | 113860 | 4/1999 |
| WO | WO-9001895 | 3/1990 |
| WO | WO-2001027855 | 4/2001 |
| WO | WO-2002082999 | 10/2002 |
| WO | 2004004557 | 1/2004 |
| WO | WO-2009032073 | 3/2009 |
| WO | WO-2013186696 | 12/2013 |
| WO | WO-2013191657 | 12/2013 |
| WO | WO-2013192166 | 12/2013 |
| WO | WO-2014116968 | 7/2014 |
| WO | WO-2014124520 | 8/2014 |
| WO | WO-2014136027 | 9/2014 |
| WO | WO-2014138280 | 9/2014 |
| WO | WO-2014160893 | 10/2014 |
| WO | 2016118534 | 7/2016 |
| WO | 2016176471 | 11/2016 |
| WO | 2016178797 | 11/2016 |
| WO | 2017019299 | 2/2017 |

OTHER PUBLICATIONS

"International Search Report and Written Opinion", Application No. PCT/US2016/029820, dated Jul. 15, 2016, 14 pages.

"Non-Final Office Action", U.S. Appl. No. 14/582,896, dated Jun. 29, 2016, 9 pages.

"Non-Final Office Action", U.S. Appl. No. 14/681,625, dated Aug. 12, 2016, 9 pages.

"Restriction Requirement", U.S. Appl. No. 14/666,155, dated Jul. 22, 2016, 5 pages.

"The Instant Blood Pressure app estimates blood pressure with your smartphone and our algorithm", Retrieved at: http://www.instantbloodpressure.com/—on Jun. 23, 2016, 6 pages.

Klabunde,"Ventricular Pressure-Volume Loop Changes in Valve Disease", Retrieved From <https://web.archive.org/web/20101201185256/http://cvphysiology.com/Heart%20Disease/HD009.htm>, Dec. 1, 2010, 8 pages.

"Final Office Action", U.S. Appl. No. 14/504,038, dated Sep. 27, 2016, 23 pages.

"International Search Report and Written Opinion", Application No. PCT/US2016/032307, dated Aug. 25, 2016, 13 pages.

"Non-Final Office Action", U.S. Appl. No. 14/518,863, dated Oct. 14, 2016, 16 pages.

"Non-Final Office Action", U.S. Appl. No. 14/666,155, dated Aug. 24, 2016, 9 pages.

"Pre-Interview Communication", U.S. Appl. No. 14/513,875, dated Oct. 21, 2016, 3 pages.

Espina,"Wireless Body Sensor Network for Continuous Cuff-less Blood Pressure Monitoring", International Summer School on Medical Devices and Biosensors, 2006, Sep. 2006, 5 pages.

"Corrected Notice of Allowance", U.S. Appl. No. 14/582,896, dated Dec. 19, 2016, 2 pages.

"Final Office Action", U.S. Appl. No. 14/681,625, dated Dec. 7, 2016, 10 pages.

"International Search Report and Written Opinion", Application No. PCT/US2016/042013, dated Oct. 26, 2016, 12 pages.

"International Search Report and Written Opinion", Application No. PCT/US2016/033342, dated Oct. 27, 2016, 20 pages.

"Non-Final Office Action", U.S. Appl. No. 14/504,121, dated Jan. 9, 2017, 13 pages.

"Notice of Allowance", U.S. Appl. No. 14/582,896, dated Nov. 7, 2016, 5 pages.

Matthews,"Venous Pulse", Retrieved at: http://www.rjmatthewsmd.com/Definitions/venous_pulse.htm—on Nov. 30, 2016, Apr. 13, 2013, 7 pages.

"Philips Vital Signs Camera", Retrieved From: <http://www.vitalsignscamera.com/> Apr. 15, 2015, Jul. 17, 2013, 2 pages.

"Cardiio", Retrieved From: <http://www.cardiio.com/> Apr. 15, 2015 App Information Retrieved From: <https://itunes.apple.com/us/app/cardiio-touchless-camera-pulse/id542891434?ls=1&mt=8>Apr. 15, 2015, Feb. 24, 2015, 6 pages.

Balakrishnan,"Detecting Pulse from Head Motions in Video", In Proceedings: CVPR '13 Proceedings of the 2013 IEEE Conference on Computer Vision and Pattern Recognition Available at: <http://people.csail.mit.edu/mrub/vidmag/papers/Balakrishnan_Detecting_Pulse_from_2013_CVPR_paper.pdf>, Jun. 23, 2013, 8 pages.

Couderc,"Detection of Atrial Fibrillation using Contactless Facial Video Monitoring", In Proceedings: Heart Rhythm Society, vol. 12, Issue 1 Available at: <http://www.heartrhythmjournal.com/article/S1547-5271(14)00924-2/pdf>, Jan. 2015, 7 pages.

He,"A Continuous, Wearable, and Wireless Heart Monitor Using Head Ballistocardiogram (BCG) and Head Electrocardiogram (ECG) with a Nanowatt ECG Heartbeat Detection Circuit", In Proceedings: Thesis, Department of Electrical Engineering and Computer Science, Massachusetts Institute of Technology Available at: <http://dspace.mit.edu/handle/1721.1/79221>, Feb. 2013, 137 pages.

Nakajima,"Development of Real-Time Image Sequence Analysis for Evaluating Posture Change and Respiratory Rate of a Subject in Bed", In Proceedings: Physiological Measurement, vol. 22, No. 3 Retrieved From: <http://iopscience.iop.org/0967-3334/22/3/401/pdf/0967-3334_22_3_401.pdf>Feb. 27, 2015, Aug. 2001, 8 pages.

Poh,"A Medical Mirror for Non-contact Health Monitoring", In Proceedings: ACM SIGGRAPH Emerging Technologies Available at: <http://affectmedia.mit.edu/pdfs/11.Poh-etal-SIGGRAPH.pdf>, 2011, 1 page.

Poh,"Non-contact, Automated Cardiac Pulse Measurements Using Video Imaging and Blind Source Separation.", In Proceedings: Optics Express, vol. 18, No. 10 Available at: <http://www.opticsinfobase.org/view_article.cfm?gotourl=http%3A%2F%2Fwww%2Eopticsinfobase%2Eorg%2FDirectPDFAccess%2F77B04D55%

(56) References Cited

OTHER PUBLICATIONS

2DBC95%2D6937%2D5BAC49A426378CO2%5F199381%2Foe%2D18%2D10%2D10762%2Ep, May 7, 2010, 13 pages.
Wang,"Exploiting Spatial Redundancy of Image Sensor for Motion Robust rPPG", In Proceedings: IEEE Transactions on Biomedical Engineering, vol. 62, Issue 2, Jan. 19, 2015, 11 pages.
"Non-Final Office Action", U.S. Appl. No. 14/599,954, dated Feb. 2, 2016, 17 pages.
"Non-Final Office Action", U.S. Appl. No. 14/504,038, dated Feb. 26, 2016, 22 pages.
"Final Office Action", U.S. Appl. No. 14/518,863, dated May 5, 2017, 18 pages.
"International Preliminary Report on Patentability", Application No. PCT/US2015/050903, dated Apr. 13, 2017, 12 pages.
"Notice of Allowance", U.S. Appl. No. 14/599,954, dated May 24, 2017, 11 pages.
"Notice of Allowance", U.S. Appl. No. 14/494,863, dated May 30, 2017, 7 pages.
"Notice of Allowance", U.S. Appl. No. 14/681,625, dated Jun. 7, 2017, 7 pages.
"Corrected Notice of Allowance", U.S. Appl. No. 14/582,896, dated Feb. 6, 2017, 2 pages.
"Corrected Notice of Allowance", U.S. Appl. No. 14/582,896, dated Feb. 23, 2017, 2 pages.
"International Preliminary Report on Patentability", Application No. PCT/US2015/043963, dated Feb. 16, 2017, 12 pages.
"International Preliminary Report on Patentability", Application No. PCT/US2015/043949, dated Feb. 16, 2017, 13 pages.
"Life:X Lifestyle eXplorer", Retrieved from <https://web.archive.org/web/20150318093841/http://research.microsoft.com/en-us/projects/lifex >, Feb. 3, 2017, 2 pages.
"Non-Final Office Action", U.S. Appl. No. 14/504,038, dated Mar. 22, 2017, 33 pages.
"Non-Final Office Action", U.S. Appl. No. 14/513,875, dated Feb. 21, 2017, 9 pages.
"Non-Final Office Action", U.S. Appl. No. 14/599,954, dated Jan. 26, 2017, 16 pages.
"Non-Final Office Action", U.S. Appl. No. 14/666,155, dated Feb. 3, 2017, 12 pages.
"Non-Final Office Action", U.S. Appl. No. 14/681,625, dated Mar. 6, 2017, 7 pages.
"Pre-Interview Communication", U.S. Appl. No. 14/494,863, dated Jan. 27, 2017, 5 pages.
"Pre-Interview Communication", U.S. Appl. No. 14/715,454, dated Apr. 14, 2017, 3 pages.
"The Dash smart earbuds play back music, and monitor your workout", Retrieved from <http://newatlas.com/bragi-dash-tracking-earbuds/30808/>, Feb. 13, 2014, 3 pages.
Palese,"The Effects of Earphones and Music on the Temperature Measured by Infrared Tympanic Thermometer: Preliminary Results", ORL—head and neck nursing: official journal of the Society of Otorhinolaryngology and Head-Neck Nurses 32.2, 2013, pp. 8-12.
"Clever Toilet Checks on Your Health", CNN.Com; Technology, Jun. 28, 2005, 2 pages.
"Final Office Action", U.S. Appl. No. 14/504,121, dated Aug. 8, 2017, 16 pages.
"Final Office Action", U.S. Appl. No. 14/715,454, dated Sep. 7, 2017, 14 pages.
"First Action Interview Pilot Program Pre-Interview Communication", U.S. Appl. No. 14/731,195, dated Aug. 1, 2017, 3 pages.
"Non-Final Office Action", U.S. Appl. No. 14/720,632, dated Jun. 14, 2017, 16 pages.
"Notice of Allowance", U.S. Appl. No. 14/513,875, dated Jun. 28, 2017, 7 pages.
"Notice of Allowance", U.S. Appl. No. 14/666,155, dated Jul. 10, 2017, 7 pages.
"Notice of Allowance", U.S. Appl. No. 14/504,038, dated Aug. 7, 2017, 17 pages.
Otto, et al., "System Architecture of a Wireless Body Area Sensor Network for Ubiquitous Health Monitoring", Journal of Mobile Multimedia; vol. 1, No. 4, Jan. 10, 2006, 20 pages.
"Apple Watch Used Four Sensors to Detect your Pulse", retrieved from http://www.theverge.com/2014/9/9/6126991 /apple-watch-four-back-sensors-detect-activity on Sep. 23, 2017 as cited in PCT search report for PCT Application No. PCT/US2016/026756 on Nov. 10, 2017; The Verge, paragraph 1, Sep. 9, 2014, 4 pages.
"International Preliminary Report on Patentability", PCT Application No. PCT/US2016/026756, dated Oct. 19, 2017, 8 pages.
"Non-Final Office Action", U.S. Appl. No. 14/518,863, dated Sep. 29, 2017, 20 pages.
"Non-Final Office Action", U.S. Appl. No. 14/699,181, dated Oct. 18, 2017, 33 pages.
"Non-Invasive Quantification of Peripheral Arterial Volume Distensibilitiy and its Non-Lineaer Relationship with Arterial Pressure", Journal of Biomechanics, Pergamon Press, vol. 42, No. 8; as cited in the search report for PCT/US2016/013968 citing the whole document, but in particular the abstract, dated May 29, 2009, 2 pages.
"Notice of Allowance", U.S. Appl. No. 14/681,625, dated Oct. 23, 2017, 8 pages.
"Pressure-Volume Loop Analysis in Cardiology", retrieved from https://en.wikipedia.org/w/index.php?t itle=Pressure-volume loop analysis in card iology&oldid=636928657 on Sep. 23, 2017; Obtained per link provided in search report from PCT/US2016/01398 on Jul. 28, 2016, Dec. 6, 2014, 10 pages.
"Written Opinion", PCT Application No. PCT/US2016/042013, dated Feb. 2, 2017, 6 pages.
"Written Opinion", PCT Application PCT/US2016/013968, dated Jul. 28, 2016, 9 pages.
"Written Opinion", PCT Application No. PCT/US2016/026756, dated Nov. 10, 2016, 7 pages.
Ishijima, "Unobtrusive Approaches to Monitoring Vital Signs at Home", Medical & Biological Engineering and Computing, Springer, Berlin, DE, vol. 45, No. 11 as cited in search report for PCT/US2016/013968 dated Jul. 28, 2016, Sep. 26, 2007, 3 pages.
"Final Office Action", U.S. Appl. No. 14/720,632, Jan. 9, 2018, 18 pages.
"Non-Final Office Action", U.S. Appl. No. 14/715,454, Jan. 11, 2018, 16 pages.
"Non-Final Office Action", U.S. Appl. No. 14/504,121, Jan. 2, 2018, 19 pages.
"Pre-Interview Office Action", U.S. Appl. No. 14/731,195, Dec. 20, 2017, 4 pages.
"Preliminary Report on Patentability", PCT Application No. PCT/US2016/032307, Dec. 7, 2017, 9 pages.
"Final Office Action", U.S. Appl. No. 14/715,454, dated Apr. 17, 2018, 19 pages.
"Final Office Action", U.S. Appl. No. 14/518,863, dated Apr. 5, 2018, 21 pages.
"Notice of Allowance", U.S. Appl. No. 14/666,155, dated Feb. 20, 2018, 5 pages.
"Notice of Allowance", U.S. Appl. No. 14/599,954, dated Mar. 15, 2018, 9 pages.
"Preliminary Report on Patentability", PCT Application No. PCT/US2016/042013, Jan. 30, 2018, 7 pages.
"Thermofocus No Touch Forehead Thermometer", Technimed, Internet Archive. Dec. 24, 2014. https://web.archive.org/web/20141224070848/http://www.tecnimed.it:80/thermofocus-forehead-thermometer-H1N1-swine-flu.html, Dec. 24, 2018, 4 pages.
"Final Office Action", U.S. Appl. No. 14/699,181, dated May 4, 2018, 41 pages.
"Final Office Action", U.S. Appl. No. 14/504,121, dated Jul. 9, 2018, 23 pages.
"First Action Interview Office Action", U.S. Appl. No. 14/731,195, dated Jun. 21, 2018, 4 pages.
"Non-Final Office Action", U.S. Appl. No. 14/720,632, dated May 18, 2018, 20 pages.
"Non-Final Office Action", U.S. Appl. No. 14/809,901, dated May 24, 2018, 13 pages.

\* cited by examiner

OPTICAL CENTRAL VENOUS PRESSURE MEASUREMENT

BACKGROUND

As part of treating patients, and more importantly patients that are critically ill, medical professionals evaluate and address patients' hemodynamics. One of the measurements that is useful to medical professionals in evaluating a patient's hemodynamics is central venous pressure (CVP), which is the blood pressure in the thoracic vena cava near the right atrium of a patient's heart. Since the CVP is essentially the same as the right atrial pressure, CVP is an important clinical measurement of the right ventricle's filling pressure. This filling pressure determines the preload of the right ventricle, which directly impacts stroke volume through the Frank-Starling mechanism. A standard first order model predicts that a change in CVP is equal to a change in volume divided by a change in venous compliance. To this extent, CVP is increased by venous blood volume or by an increase in venous tone. Such increases in CVP can indicate hypervolemia, heart failure, or respiratory problems for a patient.

Conventional techniques for measuring CVP are not without their drawbacks, however. Some conventional techniques for measuring CVP are invasive, for example, and involve inserting a catheter into the subclavian or internal jugular vein with a tip positioned in the vena cava just before the right atrium. While this invasive testing can exactly measure a person's CVP, doing so is expensive and involves significant trauma and stress on the person. On the other hand, noninvasive techniques for measuring CVP are inconsistent due to variations in the skill level and techniques across medical professionals. Generally, noninvasive CVP measurement requires the medical professional to visually estimate a peak height of pulsatile waves (rise of blood observable through pulsatile motion) in a person's external or internal jugular vein, and then to measure this height against the person's sternal angle. Such techniques are inconsistent because they rely on a difficult-to-make visual estimate, made by a particular medical professional, as to where the pulsatile wave ends and the height based on the sternal angle. Further, to make these measurements, medical professionals undergo a significant degree of training. As such, they are performed almost solely by skilled physicians, making their use outside a clinic or hospital environment cost prohibitive. The drawbacks of both the invasive and non-invasive CVP-measuring techniques render them less than ideal in many cases.

SUMMARY

This document describes optical central venous pressure measurement. To determine the central venous pressure (CVP) of a person optically, video of the person's neck is captured. By way of example, a medical professional records a video of a right side of the person's neck using a smartphone. The right side of the person's neck is preferably captured because it is where the person's external and internal jugular veins are located and those veins fill vertically based on the CVP. The right side is preferable to the left side since it is closer to the right atrium. It is also preferable to capture the internal jugular vein over the external jugular vein since it has a more direct path to the atrium. The video is then processed according to video motion amplification techniques to generate a reconstructed video of the right side of the person's neck, e.g., by an application on the smartphone of the medical professional. In the reconstructed video, the pulsatile motion of the person's venous system that occurs at the right side of their neck is visually amplified. In other words, subtle pulsatile motions that may not have been perceptible to the human eye are amplified in a manner that enables these motions to be observed. Additionally, a vertical orientation of the person's anatomy is measured, for example, using at least one of background reference features or integrated orientation sensors in the smartphone.

Using the reconstructed video, measurements are made of a distance between a peak of the amplified pulsatile motion and an anatomical feature of the person, e.g., a mandibular angle, or ear lobe of the person. The measurements are made, for example, during respiratory pauses of the person, which can be ascertained by analyzing the reconstructed video to determine the person's breathing rate. At any rate, the measured distance between the peak of the amplified pulsatile motion and the anatomical feature is combined with the vertical orientation of the anatomy and the known distance from the anatomical feature to the sternal angle to determine CVP of the person. While determining CVP from a reconstructed video in which pulsatile motion is amplified may not result in data that is as accurate as an invasive intra-heart test, for example, it requires little if any risk to the person and is easy for a medical professional to perform. Further, the techniques described herein enable determination of CVP to be made automatically and without relying on estimates made by skilled medical professionals.

This summary is provided to introduce simplified concepts concerning the techniques, which are further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and devices for optical central venous pressure measurement are described with reference to the following drawings. The same numbers are used throughout the drawings to reference like features and components.

DETAILED DESCRIPTION

Overview

Figure 1:
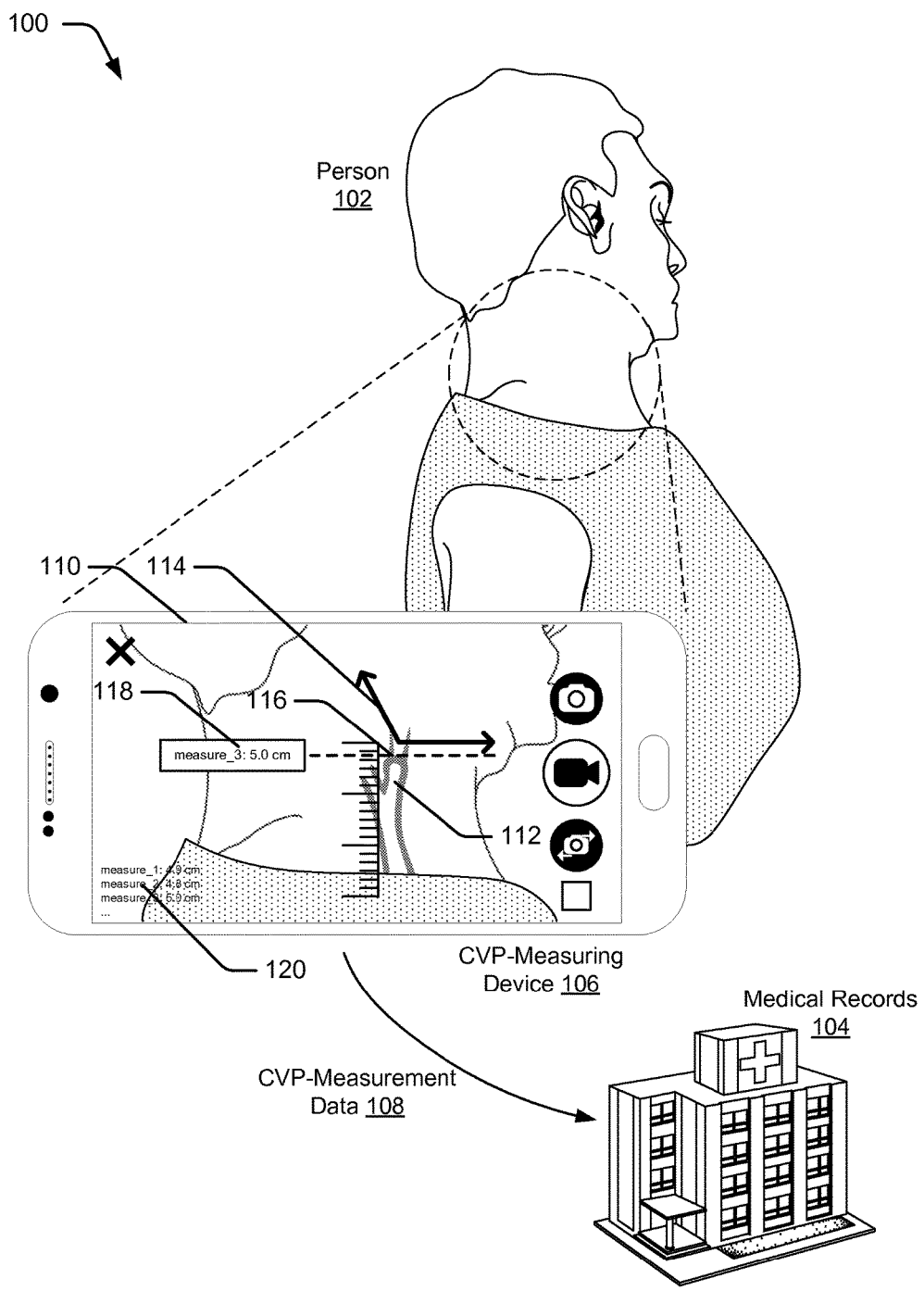
FIG. 1 illustrates an example environment in which the techniques can be implemented.

This document describes techniques using, and devices enabling, optical central venous pressure measurement. Through use of these techniques and devices, central venous pressure (CVP) for a person can be measured noninvasively and with greater reproducibility than the current clinical protocol that relies on difficult-to-make visual estimates by medical professionals. Moreover, the techniques described herein can optionally automate the measurement and reduce the role of the medical professional in determining CVP of a person to positioning a CVP-measuring device in a position where video of the person can be captured. In some embodiments, the CVP-measurement can be automated to an extent that enables a person to self-administer the measurement. Through wide application of these techniques, CVP measurements can be determined consistently and without exposing patients to invasive procedures.

By way of example, a medical professional can hold a CVP-measuring device, such as a smartphone configured with a video camera and a CVP-measuring application, to capture video of a right side of a person's neck. The captured video can then be processed by the application using one or more video motion amplification techniques, the result of which is a reconstructed video in which pulsatile motions of the person's venous system that occur in the right side of their neck are visually amplified. In one example, this reconstructed video, which is motion enhanced and optionally time stretched (e.g., slow-motion), can simply be used by the medical professional to manually identify the peak and make the CVP-measurement using the current clinical protocols. In at least some implementations, the CVP-measurement can be automated, as described herein.

Using the reconstructed video, components of the application can measure a distance between a peak of the visually-amplified pulsatile motions and an anatomical feature of the person, e.g., the person's mandibular angle. If the person's orientation is allowed to vary, the CVP-measuring device can also ascertain a vertical orientation of the person's anatomy during the measurement, such as through internal orientation sensors of the CVP-measuring device or using background reference objects. Based on the distance between a peak of a visually-amplified pulsatile motion and the anatomical feature along with the vertical orientation of the person, CVP can be determined. By making a one-time patient-specific calibration measurement of the distance between the person's anatomical feature and the standard clinical reference feature (e.g., the person's sternal angle), the CVP can be translated into the standard clinical reference absolute measurement. The CVP can then be presented to the medical professional in a user interface, for example, on a display of the smartphone of the medical professional. In some cases, the user interface may display the reconstructed video and an overlay that presents information, including the determined CVP, to the medical professional.

Thus, with the small effort of holding the device in a position to record pulsatile motion in the person's venous system, a consistent assessment of CVP can be made in a relatively short amount of time. When performed on a repeated basis and over a period of time (e.g., every few hours for a day, days, or weeks), this act can be used to determine a trend of the person's CVP. Consider that, over the course of treatment involving intravenous fluid resuscitation, the techniques, using videos captured with the CVP-measuring device, determine that the person's CVP has remained at a level indicative of normal blood flow. Using such techniques, medical professionals may avoid invasive CVP-measuring procedures, thereby likely reducing the chances of injury from the trauma associated with those procedures.

This is but one simple example of ways in which optical central venous pressure measurement can be performed, other examples and details are provided below. This document now turns to an example environment that references an example of portions of a person's anatomy pertinent to measuring CVP, after which example optical central venous pressure measurement devices and methods, and an example computing system are described.

Example Environment

FIG. 1 is an illustration of an example environment 100 in which optical central venous pressure measurement can be employed. Environment 100 illustrates a person 102 that is the subject of the central venous pressure (CVP) measuring, as well as medical records 104 that, in some cases, store results of the optically measured CVP. This example employs CVP-measuring device 106 that is capable of optically measuring CVP. In the particular example of FIG. 1, the CVP-measuring device 106 is configured as a smartphone, however, other configurations are contemplated. Other configurations of the CVP-measuring device 106 for optically measuring CVP are illustrated in later figures.

CVP-measurement data 108 is communicable from the CVP-measuring device 106 to other entities, such as a service provider that stores the medical records 104, some other computing device remote from the CVP-measuring device (not shown), and so on. The CVP-measurement data 108 can include data indicative of CVP determined by the CVP-measuring device 106. Alternately or additionally, the CVP-measurement data 108 can include raw video captured by the CVP-measuring device 106 to determine CVP, reconstructed video that results from processing the captured video according to one or more video motion amplification techniques, measurements of a distance between pulsatile waves and an anatomical feature of the person 102, and so forth. Since each of these different types of data (which, in effect, represent different portions in the process of determining CVP from captured video) can be communicated to remote computing devices, the different portions of the CVP-determining process can be performed at various computing devices. By so doing, the computing burden of determining the CVP from the captured video is capable of being offloaded from the CVP-measuring device 106. Additionally, in the case of home health care or remote telemedicine, communication of the CVP-measurement data 108 enables the measurements to be reviewed for accuracy remotely by a trained medical professional.

Generally, the CVP-measuring device 106 is capable of capturing video of the person 102. By way of example, the CVP-measuring device 106 captures video of the person using a camera that is included as part of the CVP-measuring device 106. After processing the captured video, the CVP-measuring device 106 is capable of determining the person 102's CVP from the reconstructed video that results from the processing, as described herein below.

Figure 2:
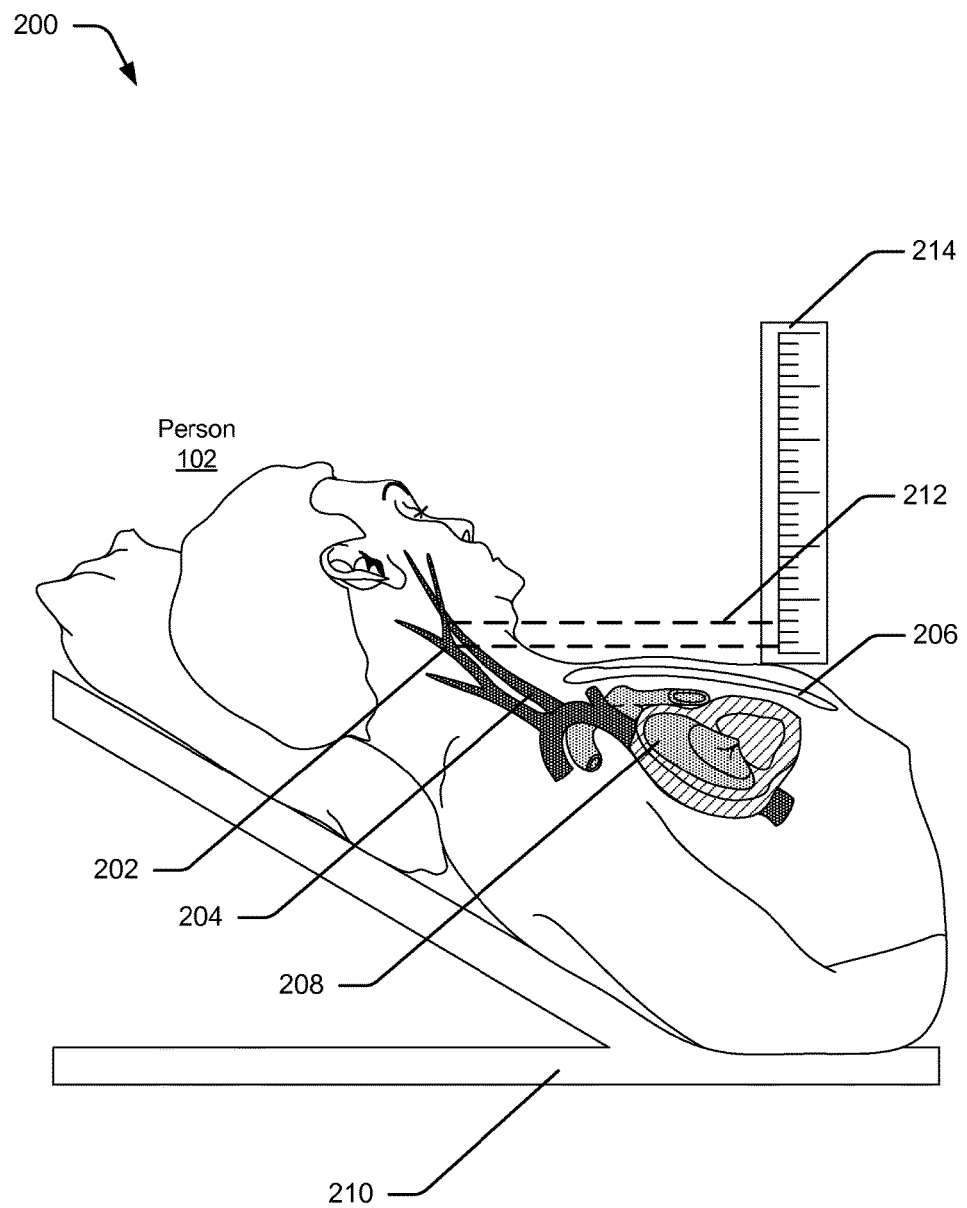
FIG. 2 illustrates an example of a person and portions of their cardiovascular system pertinent to central venous pressure (CVP) measurement.

For context, consider FIG. 2, which illustrates a person and portions of their cardiovascular system that are pertinent to CVP measurements. View 200 shows the person 102's external jugular vein 202, internal jugular vein 204, and sternal angle 206. The view 200 also shows the right atrium 208 of the person 102's heart.

Using conventional techniques for assessing CVP noninvasively, the person 102 is placed supine in bed 210. In some cases, a tangential light source is used to generate shadows and make venous motion more apparent. The head of the bed 210 is raised in increments so that it is angled at thirty, forty-five, sixty, and ninety degrees. The pulsatile peak (rise of blood observed through pulsatile motion) is based on the vertical distance above the right atrium, so as the head and neck become higher at steeper angles, the peak drops. The medical professional determines which angle has the best visible peak marker, with steeper angles preferred, and then the venous pressure 212 is determined. To do so, measuring device 214 is placed on the sternal angle 206 of the person 102, and the peak height of pulsatile waves (rise of blood observed through pulsatile motion) observed in the external or internal jugular vein, 202 or 204 respectively, is measured. This measurement thus corresponds to the vertical distance between the sternal angle 206 and the point at which the observer estimates the pulsatile motion to have peaked in the external or internal jugular vein, 202 or 204 respectively. Consequently, these techniques rely, in large part, on where the observer (e.g., a medical professional) estimates the pulsatile motion to have peaked.

Even assuming that a medical professional is capable of accurately and consistently estimating the point at which pulsatile motions peak, some pulsatile motions are so subtle that they are imperceptible to the human eye. Unlike conventional noninvasive CVP-measuring techniques, the techniques described herein amplify the human imperceptible motion to make it visible. Further, when the measuring is performed by components of the CVP-measuring device 106, these techniques do not rely on an observer to estimate where pulsatile waves observed in the person 102's neck peaked. Instead, the CVP-measuring device 106 determines CVP from a reconstructed video of the person 102 in which pulsatile motion is visually amplified. Consequently, the involvement of medical professionals in determining CVP may be reduced to simply placing the CVP-measuring device 106 in a position where video of the right side of the person 102's neck can be captured.

As shown with the example environment 100, the CVP-measuring device 106 is capable of displaying a user interface 110 to present reconstructed video in which pulsatile motion occurring in the person 102's neck is visually amplified. The user interface 110 includes visually-amplified pulsatile motion 112, for example, which is not shown on the person 102. Thus, the example environment 100 represents a scenario in which the pulsatile motion may be imperceptible to the human eye but is amplified according to one or more video motion amplification techniques to be visible in the reconstructed video. Additionally, playback of the reconstructed video can be time stretched (e.g., so that it is played back in slow motion) to allow for easier identification of the peak height of pulsatile waves and identification of a time interval that is directly before atrial contraction during which to make the measurement. The user interface 110 also includes several indications overlaying the reconstructed video, including an indication of the anatomical feature 114—in this case the mandibular angle, a line 116 indicative of a peak of a pulsatile motion along with a perpendicular ruler that indicates vertical orientation and distance, a measurement 118 corresponding to the peak of the visually-amplified pulsatile motion 112, and previous measurements 120 corresponding to peaks of visually-amplified pulsatile motions that were previously observed in the reconstructed video. Optionally, the patient's heart rate and respiration rate may also be shown in the user interface 110. In the case of use by minimally trained personnel, the user interface 110 can present anatomical guidance overlays to help guide proper orientation of the camera. By comparing the measurement 118 and the previous measurements 120 associated with a video captured at one time to those associated with a video captured at an earlier time, a trend can be determined for the person 102's CVP.

Figure 3:
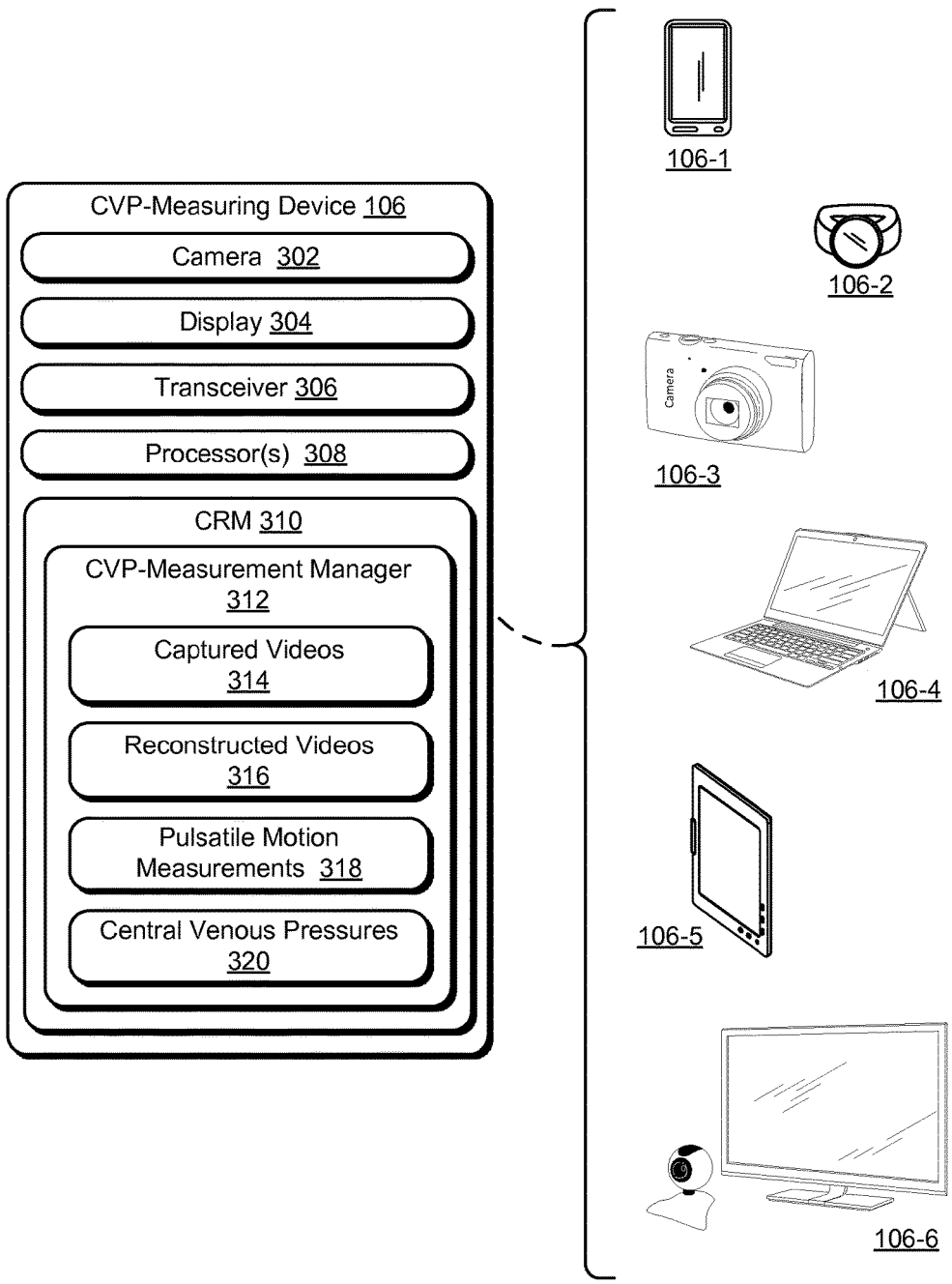
FIG. 3 illustrates an example CVP-measuring device of FIG. 1.

With regard to the example CVP-measuring device 106 of FIG. 1, consider a detailed illustration in FIG. 3. The CVP-measuring device 106 can be one or a combination of various devices, here illustrated with six examples: a smartphone 106-1, a computing watch 106-2, a digital camera 106-3, a laptop 106-4, a tablet computer 106-5, and a desktop computer coupled to an external camera device 106-6 though other computing devices and systems, such as a netbook or a specialized imaging device with a particular configuration of CVP-measurement sensors may also be used. As noted above, in some embodiments the techniques operate, at least in part, through a remote computing device. The remote computing device can be configured as a server, for example. In such cases, some computing can be forgone locally, e.g., through a communication device having limited computing operations or even directly from CVP-measuring devices 106 to the server.

The CVP-measuring device 106 includes or is able to communicate with a camera 302, a display 304 (five are shown in FIG. 3), a transceiver 306, one or more processors 308, and computer-readable storage media 310 (CRM 310). The transceiver 306 is capable of sending and receiving data directly or through a communication network, such as CVP-measurement data 108 from devices 106 through a local area, wide area, personal area, cellular, or near-field network.

The camera 302 represents functionality of the CVP-measuring device 106 to capture video of a scene, such as one that includes the person 102. In addition to capturing video, the camera 302 may be capable of capturing still images, zooming in or out to capture video and still images, and the like. With reference to the example environment 100, the camera 302 may be included in the CVP-measuring device 106 on a side opposite the display presenting the user interface 110. In this way, the user interface 110 can be used as a viewfinder for the camera 302. In some embodiments, the viewfinder can be disposed on the same side of the CVP-measuring device 106 as the camera, facilitating self-assessment. The CVP-measuring device 106 may also be configured with additional cameras, or the camera 302 configured with functionality in addition to capturing video and images. By way of example, the CVP-measuring device 106 may be configured to include hyperspectral cameras, e.g., visual and infrared. Hyperspectral cameras can be used to improve the ability of the CVP-measuring device 106 to locate veins and arteries of interest and monitor pulsatile motion. The CVP-measuring device 106 may also be configured to include a dedicated depth-sensing camera and a high-frame rate camera. A dedicated depth sensing camera can be used to increase sensitivity to motion and a high-frame rate camera can be used to improve temporal recording of the pulsatile waveforms.

The CVP-measuring device 106 can be configured with still other components to aid in detecting pulsatile motion, visually amplifying the pulsatile motion, and measuring the peak of the pulsatile motion. By way of example, the CVP-measuring device 106 can be configured with lasers or light emitting devices that emit structured light to enable a greater degree of sensitivity in motion detection. The CVP-measuring device 106 can also be configured to use tangential light sources to enhance the motion through changes in shadowing that improve a contrast of the motion relative to other portions of the person 102 (e.g., other portions of their skin). The CVP-measuring device 106 may be configured with various combinations of optical components without departing from the spirit or scope of the techniques described herein.

The CRM 310 includes CVP-measurement manager 312, which includes or has access to captured videos 314, which are output by the camera 302. The CRM 310 also includes reconstructed videos 316 which are generated by processing the captured videos 314 according to one or more video motion amplification techniques. The captured videos 314 are processed according to these techniques, for example, to visually amplify pulsatile motions captured by the original videos. Further, the CRM 310 includes or has access to pulsatile motion measurements 318 and central venous pressures 320 (CVPs 320). The pulsatile motion measurements 318 represent measurements that are made by the CVP-measurement manager 312 of the visually-amplified pulsatile motions in the reconstructed videos 316. The CVPs 320 represent the determinations of central venous pressure, including temporal waveforms, that are made from the pulsatile motion measurements 318.

The CVP-measurement manager 312 represents functionality to employ the camera 302 to capture video in conjunction with a session for determining the CVP of the person 102. As used herein, the term "session" refers to a period of time during which the CVP-measuring device 106 captures video of the person 102 for the purpose of determining their CVP. Generally, the length of a session corresponds to an amount of time that the camera 302 is employed to capture video of the person 102 that is sufficient to make the pulsatile motion measurements 318 to determine the CVPs 320. In some embodiments, the CVP-measuring device 106 is capable of alerting a medical professional using the CVP-measuring device 106 when a sufficient amount of video has been captured and the session can be ended. By way of example, the CVP-measuring device 106 can be configured to alert the person 102 audibly, such as by beeping, visually, such as by causing an indication to be presented on the user interface 110, and/or by touch, such as by vibrating.

In one example, the CVP-measurement manager 312 employs the camera 302 to capture video of a right side of the person 102's neck. As shown in FIG. 2, this is where the external and internal jugular veins, 202 and 204 respectively, of the person 102 are located. Accordingly, the right side of the person 102's neck is where pulsatile motions used to determine the CVPs 320 can be observed. Some pulsatile motions occurring on the right side of the person 102's neck may be too subtle to be perceptible by a medical professional who views the captured videos 314, for example, when the person 102 is obese and their external and internal jugular veins lie deep underneath their skin. These motions can be detected and amplified, however, through the application of video-processing techniques.

The CVP-measurement manager 312 also represents functionality to process the captured videos 314 to generate the reconstructed videos 316, in which pulsatile motions of the person 102's venous system are amplified. To do so, the CVP-measurement manager 312 is capable of applying one or more video motion amplification techniques to the captured videos 314. The result of such techniques is to amplify motions (e.g., pulsatile motions) from the captured videos 314 that are imperceptible to the human eye so that they are visible to the human eye in the reconstructed videos 316. Such techniques are also effective to improve a contrast and a signal-to-noise ratio of pulsatile motion due to the venous system for downstream processing and analysis by the CVP-measurement manager 312.

As part of applying the one or more video motion amplification techniques to a particular captured video, the CVP-measurement manager 312 spatially decomposes the video into different spatial frequency bands. The CVP-measurement manager 312 then applies temporal filters to filter for pulsatile motions at the different frequency bands. The parameters of the temporal filter can be set automatically by first measuring the heart rate of the person 102, such as by sensing color changes in the person 102's skin due to arterial blood volumes (remote photoplethysmogram) or subtle body movements created by cardiac motion or arterial blood movement. The heart rate and subtle body movements may be detected by the CVP-measuring device 106 or provided to the CVP-measurement manager 312 by an external device. The CVP-measurement manager 312 can then use the person 102's heart rate or motions to select specific frequency bands and harmonics for motion amplification. The CVP-measurement manager 312 is also capable of using the selected frequency bands and harmonics for time correlation averaging to improve signal-to-noise ratios. Based on the different spatial frequency bands in which the pulsatile motions are observed, the CVP-measurement manager 312 is capable of visually amplifying the pulsatile motions.

By way of example, the CVP-measurement manager 312 may visually amplify the pulsatile motions using amplified phase differences to magnify (or attenuate) the pulsatile motions in a sequence, or by modifying the phases of coefficients with an amount for each frame. Alternately, the CVP-measurement manager 312 may visually amplify the motions by directly modifying pixels of the captured videos 314 to result in the reconstructed videos 316. Additional inputs to the video motion amplification techniques can include hyperspectral images, when available, for improved contrast in identifying the person 102's vasculature or images from previous measurements that guide regions of interest. Indications of these spatial regions enable them to receive differential processing algorithms to further enhance potential motion.

When the captured videos 314 are processed according to such techniques, the CVP-measurement manager 312 is capable of generating, and thus displaying, the reconstructed videos 316 in real time. By "real time" it is meant that the delay between a motion occurring, which a medical professional viewing the person 102 can observe, and presentation of the visually-amplified motion on the display 304 in a reconstructed video is imperceptible or nearly imperceptible to the medical professional. Consequently, the reconstructed videos 316 can be displayed on the display 304 as part of the user interface 110 while the camera 302 is being used to capture video. In this way, the user interface 110 presented via the display 304 can act as a viewfinder for the camera 302. It should be noted that other video motion amplification techniques may be applied to generate the reconstructed videos 316 without departing from the spirit or scope of the techniques described herein.

In addition to real-time display, the CVP-measurement manager 312 is also capable of playing back the reconstructed videos at other speeds or at different times. For example, the CVP-measurement manager 312 can enable a reconstructed video to be played back in slow motion. The user interface 110 may enable a user of the CVP-measuring device 106 to choose a speed at which to playback the reconstructed video, e.g., ½ speed, ¼ speed, ⅛ speed, and so on. The user interface 110 may also include controls that enable the user to pause the reconstructed video, skip forward or backward (at different speeds), return to a live feed, and so forth. By playing back the reconstructed video in slow motion and allowing it to be paused at different locations during playback, the user interface 110 can enable a medical professional to manually measure the distance between the peak of a pulsatile wave and the anatomical feature of the person 102. To enable such measuring, the user interface 110 may include a perpendicular ruler as shown in FIG. 1, which can indicate a vertical orientation and have markers for measuring the distance.

The user interface 110 may also include other capabilities and graphics not shown in FIG. 1. For example, a waveform of the pulsatile motion may be generated and displayed via the user interface 110. As part of doing so, the pulsatile motion may be extracted along a line coincident with the venous anatomy. The pulsatile motion may be displayed like an ultrasound m-mode image. Doing so can aid both in visualizing the pulsatile motion and in measuring it. By way of example, the waveform can be analyzed by the CVP-measurement manager 312 to determine when "a-waves" occur in the waveform. The CVP-measurement manager 312 can then select the height of the pulsatile motion just before an a-wave occurs to make the CVP-measurement.

Regardless of the particular motion amplification techniques applied, the pulsatile motions captured in the captured videos 314 can be visually amplified so that they are not only made visible to the human eye in the reconstructed videos 316, but are also measurable by the CVP-measurement manager 312. To measure a given pulsatile motion of the person 102's venous system that occurs in the right side of their neck, the CVP-measurement manager 312 may determine a frame of a corresponding reconstructed video in which a visually-amplified pulsatile motion has reached a peak height. The CVP-measurement manager 312 may then, in the frame, measure a distance between the peak height of the visually-amplified pulsatile motion and an anatomical feature of the person 102, e.g., a mandibular angle of the person 102, their ear lobe, and so forth. Generally, the anatomical feature of the person 102, against which the distance is measured, is one that remains visible throughout a portion of the reconstructed video during which the measurements are made and remains substantially motionless with respect to the pulsatile region of interest. One example anatomical feature, the mandibular angle, is capable of providing a strong feature that can be used to track motion and compensate for global movements of the person 102 or the camera 302. The CVP-measurement manager 312 is also capable of tracking movement in the angle between the mandible and neck to further increase motion accuracy. To compensate for the effects of gravity, the CVP-measurement manager 312 determines an orientation of the person 102 relative to a vertical orientation, e.g., based on background reference features or sensors integrated in the CVP-measuring device 106. The CVP-measurement manager 312 combines the determined vertical orientation with the measured distance between the amplified pulsatile motion and the anatomical feature for the person 102.

Changes in thoracic pressure that result from breathing can cause the level of a pulsatile wave in the person 102's venous system (observable through pulsatile motion) to rise and fall. To obtain consistent measurements for determining the CVPs 320, the CVP-measurement manager 312 is capable of making the measurements at a same point in the person 102's respiratory phase, such as natural respiratory pauses of the person 102. To do so, the CVP-measurement manager 312 analyzes the reconstructed videos 316 to determine a breathing rate of the person 102. Through the analysis, the CVP-measurement manager 312 is capable of determining periods when inhalations, exhalations, and respiratory pauses occur. Given this information, the CVP-measurement manager 312 measures the distance between the peak height of the visually-amplified pulsatile motions and the anatomical feature during a same point in the person's respiratory phase. Further, the CVP-measurement manager 312 may avoid making these measurements during periods when inhalations and exhalations are determined to occur. Additionally, the CVP-measurement manager 312 can increase the confidence level of CVP-measurement by observing the expected changes in CVP during the phases of the respiratory cycle. In other words, the CVP-measurement can be confirmed by measuring a change in CVP-measurements that match the respiration rate of the person 102.

Once a distance between a peak height of a visually-amplified pulsatile motion and the person's anatomical feature is measured, the CVP-measurement manager 312 can store data indicative of that measurement as a pulsatile motion measurement 318. Since several measurable pulsatile motions may occur while a video is being captured, the CVP-measurement manager 312 may make multiple pulsatile motion measurements 318 using a single reconstructed video 316. To this extent, the CVP-measurement manager 312 may perform a statistical analysis on the pulsatile motion measurements made in association with a single reconstructed video 316. In so doing, the CVP-measurement manager 312 may select a pulsatile motion measurement 318 that will result in a CVP determination that best represents the person 102's CVP at the time the associated video was captured. In addition or alternately, the CVP-measurement manager 312 may compute, from the observed pulsatile motion measurements 318, an average or representative pulsatile motion measurement from which to determine the person 102's CVP.

From the pulsatile motion measurements 318, the CVP-measurement manager 312 can determine the CVPs 320. CVP is generally determined with reference to the person 102's right atrium 208. In the above-discussed conventional techniques for noninvasively determining CVP, the determination of CVP assumes that the distance between the person 102's right atrium 208 and sternal angle 206 is an arbitrary distance of five centimeters. To this extent, the CVP-measurement manager 312 can determine CVPs 320 from the pulsatile motion measurements 318 by relating the person 102's anatomical feature to their right atrium 208. When the anatomical feature used corresponds to the person 102's mandibular angle, for example, the CVP-measurement manager 312 may assume that the distance between the person 102's mandibular angle and their right atrium 208 corresponds to some arbitrary distance. By way of example, the CVP-measurement manager 312 can employ the camera 302 to make a calibration measurement from the anatomical feature to the sternal angle or right atrium. The user interface 110 may also enable the calibration measurement to be entered manually, such that the medical professional can manually measure the distance between the anatomical feature and the sternal and then input that distance into the user interface 110. Alternately, the CVP-measurement manager 312 may employ some other techniques to determine an actual distance between the person 102's anatomical feature and their sternal angle or right atrium 208. In any case, once the CVP-measurement manager 312 determines CVPs from the pulsatile motion measurements 318, data indicative of the determined CVPs may be stored as CVPs 320.

The CVP-measurement manager 312 is capable of determining CVPs 320 in ways other than measuring a distance between a peak height of pulsatile motions that occur on the person 102's neck and a selected anatomical feature. The CVP measurement manger 312 can also determine CVP using videos in which the person 102 slowly raises their hands. To do so, the CVP measurement manger 312 processes the videos according to the one or more motion amplification techniques discussed above. In the resulting reconstructed video, motion detected in the captured video that results from at least one of veins collapsing in the person 102's arms or a change in pulse is amplified. Using the reconstructed video, the CVP-measurement manager 312 measures an angle and a height of the person 102's raised hands relative to their heart. The CVP-measurement manager 312 may make this measurement, for example, in a frame that corresponds to when the person 102's veins collapsed or when the pulse changed. Based on the measured angle and height of the hands, the CVP-measurement manager 312 is capable of determining the person 102's CVP.

As discussed above, the captured videos 314, the reconstructed videos 316, the pulsatile motion measurements 318, and the CVPs 320 can be associated with times. One of the captured videos 314, for example, can be associated with a time when it was captured, e.g., the CVP-measuring device 106 can associate a timestamp with the captured video. The reconstructed video 316 that is generated from this captured video can also be associated with the time. In a similar manner, the pulsatile motion measurements 318 made using the reconstructed video 316, and the CVPs 320 determined from those pulsatile motion measurements 318, may also be associated with the time. A second captured video that is captured at a different time, say after the one captured video, can be associated with a different time. Accordingly, the reconstructed video 316 generated from this second captured video, the pulsatile motion measurements 318 made using that reconstructed video 316, and the CVPs 320 determined from those pulsatile motion measurements 318, can be associated with the different time. In so doing, the pulsatile motion measurements 318 and the CVPs 320 can be compared over time.

Based on a comparison of CVPs determined at different times, a trend in the person 102's CVP can be determined. For example, CVPs determined every four hours over the course of two days can be compared to determine a trend in the person 102's CVP for the two-day period. The CVPs 320 determined over the two-day period may indicate an increase or decrease in the person 102's CVP. Based on the trend (e.g., the determined increase or decrease), a medical professional may be able to make other assessments regarding the person 102, such as to the effectiveness of treatments being administered to the person 102. The comparison of the CVPs 320 may also enable a trend in the person 102's cardiovascular health to be determined. The person 102's CVP will rise when the right ventricle is failing, for example.

In addition to determining CVP, the reconstructed videos 316 can be analyzed to measure markers in pulsatile waveforms of the CVP. In addition to cardiac timing parameters, the pulsatile waveforms can also be analyzed to check for abnormalities. As mentioned above, a waveform of pulsatile motion can be generated by the CVP-measurement manager 312 by extracting pulsatile motion along a line coincident with the venous anatomy. Example clinical indicators include tracking atrial-to-ventricular contraction, indicated by an "a-wave", or checking for tricuspid regurgitation visible in "v-waves" going back through the veins. The term "a-wave" refers to a venous pressure pulse due to atrial contraction while the term "v-wave" refers to a wave that arises from pressure produced when the blood that is filling the right atrium 208 of the person 102 comes up against a closed tricuspid valve. Missing a-waves would indicate atrial fibrillation, while elevated v-waves indicate the potential presence of tricuspid regurgitation. The reconstructed videos 316 are also analyzable to detect other backpressure waves that result from valves in the person 102's heart closing, and these timing markers provide insights into cardiac timing of the person 102.

By enabling CVP to be measured automatically, the CVP-measuring device 106 can be used to enable telemedicine. In other words, the person 102 may be able to stay at home and receive health care. Not only may data indicative of the CVPs 320 be communicated to a medical professional associated with the person 102, but the captured and reconstructed videos, 314 and 316 respectively, can also be communicated to the medical professional to enable them to remotely analyze the person 102's CVP. Further, the techniques described herein enable home or nursing care to be provided by medical professionals other than physicians.

These and other capabilities, as well as ways in which entities of FIGS. 1-3 act and interact, are set forth in greater detail below. These entities may be further divided, combined, and so on. The environment 100 of FIG. 1 and the detailed illustrations of FIGS. 2 and 3 illustrate some of many possible environments capable of employing the described techniques.

Example Methods

Figure 4:
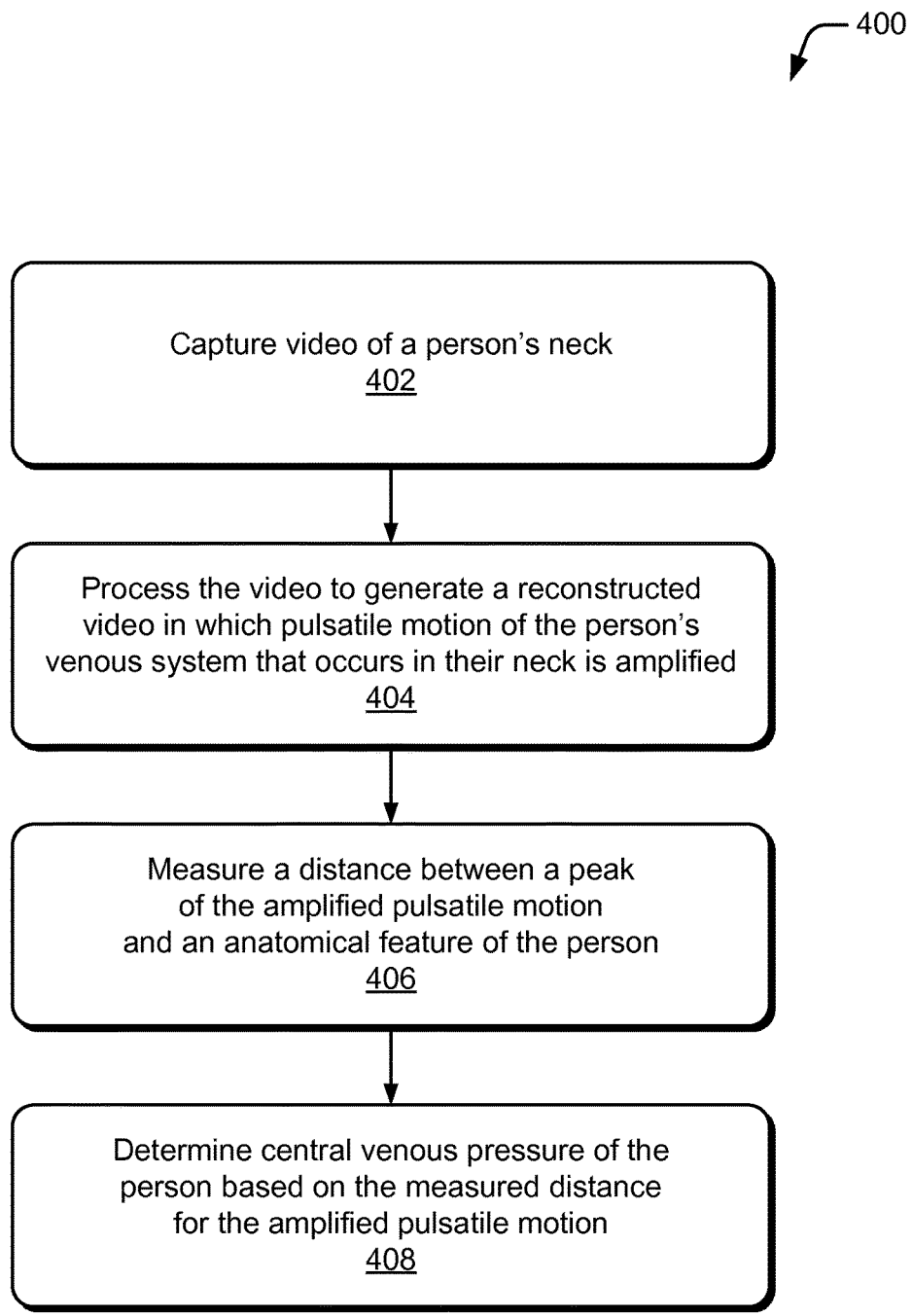
FIG. 4 illustrates a method to optically measure CVP with a video recording of a right side of a person's neck.
Figure 5:
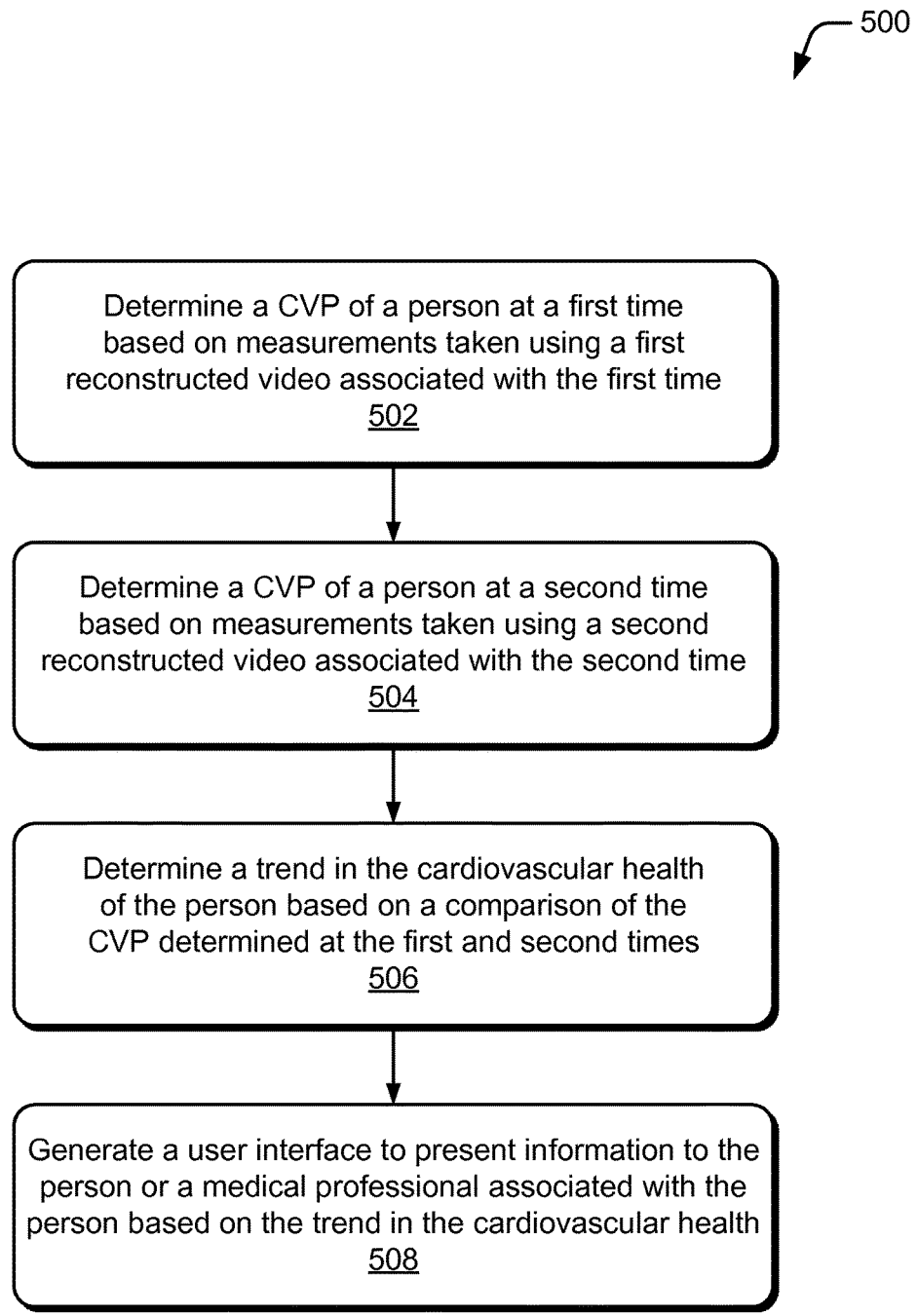
FIG. 5 illustrates a method to determine a trend in a person's cardiovascular health using multiple CVP measurements determined at different times with different video recordings.

FIGS. 4 and 5 depict methods enabling or using optical central venous pressure measurement. These methods are shown as sets of blocks that specify operations performed but are not necessarily limited to the order or combinations shown for performing the operations by the respective blocks. In portions of the following discussion reference may be made to environment 100 of FIG. 1 and entities detailed in FIGS. 2 and 3, reference to which is made for example only. The techniques are not limited to performance by one entity or multiple entities operating on one device.

FIG. 4 depicts method 400, which describes manners in which to optically measure central venous pressure (CVP) of a person with a video recording of a right side of their neck.

At 402, video of a person's neck is captured. By way of example, the CVP-measurement manager 312 employs the camera 302 of the CVP-measuring device 106 to capture video of the right side of the person 102's neck. The CVP-measurement manager 312 may do so, for example, in response to a touch selection by a user (e.g., a medical professional) of a button to initiate a determination of CVP. This button may be generated and presented by a vitals-monitoring application of the CVP-measuring device 106. The CVP-measurement manager 312 may also employ the camera 302 to capture video of the person 102 in response to other initiation actions. For example, the CVP-measuring device 106 may be set up in a fixed position relative to the person 102, such as on a tripod, and automatically initiate a determination of the person 102's CVP at predetermined intervals. When the CVP-measuring device 106 is set up in this way, the person 102's CVP may be determined without any user interaction other than to position the CVP-measuring device 106 initially.

At 404, the captured video is processed according to one or more video motion amplification techniques to generate a reconstructed video in which pulsatile motion that occurs in the person 102's venous system is amplified. As a video is being captured, for instance, the CVP-measurement manager 312 applies the one or more video motion amplification techniques to generate a corresponding reconstructed video. In the reconstructed videos 316, the pulsatile motions captured in the captured videos 314 are amplified not only so that they are visible to the human eye, but also so that they are measurable by the CVP-measurement manager 312. The motions that are visually amplified may appear different in color than in the captured videos 314, or be enhanced in some other way so that they are made visible.

At 406, a distance between a peak of the amplified pulsatile motion and an anatomical feature of the person is measured. For example, the CVP-measurement manager 312 determines a frame of the reconstructed video in which a pulsatile motion has peaked. The CVP-measurement manager 312 then measures a distance in that frame between the peak of the visually-amplified pulsatile motion and the anatomical feature, which as discussed above may be the mandibular angle or the ear lobe. Although mandibular angle and ear lobe are discussed herein throughout, the distance may be measured relative to an anatomical feature other than the mandibular angle or ear lobe. By way of example, the CVP-measurement manager 312 may select another anatomical feature relative to which measurements can be made. Selection of the anatomical feature may be based on the anatomical feature remaining visible and substantially motionless while the measurements are being made.

At 408, CVP of the person is determined based on the measured distance for the processing-amplified pulsatile motion. The CVP-measurement manager 312, for example, determines the CVPs 320 based on the pulsatile motion measurements 318. The CVP-measurement manager 312 may determine a CVP for each of the pulsatile motion measurements 318. Alternately, the CVP-measurement manager 312 may use just one pulsatile motion measurement to determine the person 102's CVP for a particular captured video 314. As noted above, the CVP-measurement manager 312 may do so by selecting a pulsatile motion measurement 318 that will result in a CVP determination that best represents the person 102's CVP at the time the associated video was captured. The CVP-measurement manager 312 may also compute, from the observed pulsatile motion measurements 318, an average or representative pulsatile motion measurement from which to determine the person 102's CVP.

FIG. 5 depicts method 500, which describes manners in which to determine a trend in a person's cardiovascular health using multiple CVP measurements determined at different times with different video recordings.

At 502, a CVP of a person is determined at a first time based on measurements taken using a first reconstructed video associated with the first time. By way of example, the CVP-measurement manager 312 employs the camera 302 to capture a video of the person 102 at a first time, as in act 402 of FIG. 4. The CVP-measurement manager 312 then processes the video captured at the first time to generate a reconstructed video as in act 404, measures a distance between a peak of a visually-amplified pulsatile motion in the reconstructed video and an anatomical feature of the person 102 as in act 406, and determines the CVP for the person as in act 408. The person 102's CVP determined from this reconstructed video may be stored as one of the CVPs 320 with an indication that it is associated with the first time.

At 504, a CVP of the person is determined at a second time based on measurements taken using a second reconstructed video associated with the second time. For example, the CVP-measurement manager 312 again employs the camera 302 to capture another video of the person 102, but at the second time which is after the first time. The CVP-measurement manager 312 then processes this other video captured at the second time to generate a second reconstructed video as in act 404, measures a distance between a peak of a visually-amplified pulsatile motion in the second reconstructed video and an anatomical feature of the person 102 as in act 406, and determines the CVP for the person as in act 408. The person 102's CVP determined from the second reconstructed video may be stored as one of the CVPs 320 with an indication that it is associated with the second time.

At 506, a trend in the cardiovascular health of the person is determined based on a comparison of the CVP determined at the first and second times. By way of example, the CVP-measurement manager 312 accesses the CVP determined in act 502 and the CVP determined in act 504 from storage, e.g., medical records stored in association with the person 102. The CVP-measurement manager 312 then compares those two CVPs. The comparison may indicate an increase or decrease in the person 102's CVP from the first time to the second time. A trend in the cardiovascular health can be determined from the increase or decrease in the CVP, such as hypervolemia, heart problems, or respiratory problems for a person. Alternately, such a trend can indicate whether dietary, pharmaceutical, or intravenous treatment being administered to the person 102 is effective.

At 508, a user interface is generated to present information to the person or a medical professional associated with the person based on the trend in the cardiovascular health. For example, the CVP-measurement manager 312 can generate a user interface that includes an indication of a determined CVP. The determined CVP can be presented overlaying a reconstructed video in which pulsatile motions are visually amplified as discussed above. The CVP-measurement manager 312 can also generate a user interface for an associated medical professional that indicates a trend in CVP (increase or decrease) and what the increase or decrease can indicate, e.g., hypervolemia, heart failure, and so on. When the trend in CVP indicates a potential negative cardiac health condition, the user interface can be generated for the person 102 to advise them to seek immediate medical attention. When the trend in CVP indicates a positive cardiac health condition, the user interface can be generated for the person 102 to indicate improvement in heart health.

The preceding discussion describes methods relating to optical central venous pressure measurement. Aspects of these methods may be implemented in hardware (e.g., fixed logic circuitry), firmware, software, manual processing, or any combination thereof. These techniques may be embodied on one or more of the entities shown in FIGS. 1-3 and 6 (computing system 600 is described in FIG. 6 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 6:
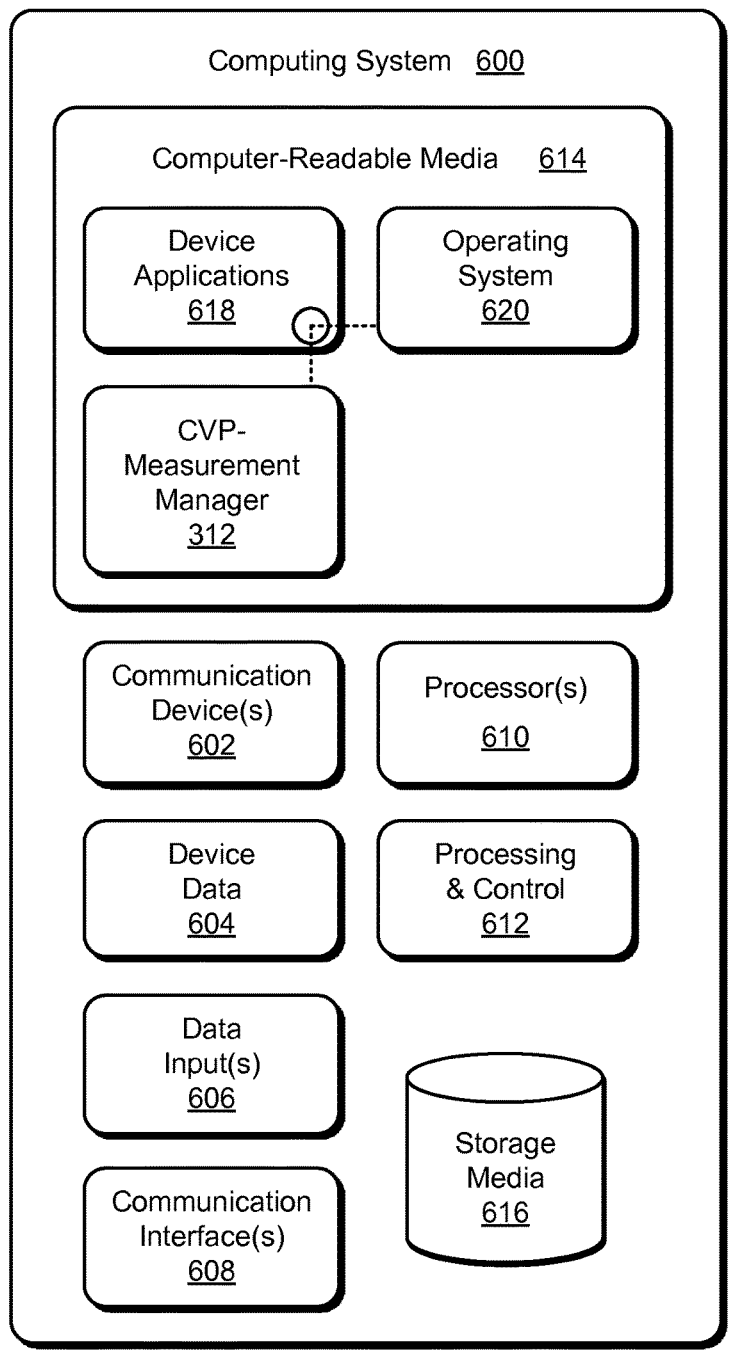
FIG. 6 illustrates an example computing system embodying, or in which techniques may be implemented that enable use of, optical central venous pressure measurement.

FIG. 6 illustrates various components of example computing system 600 that can be implemented as any type of client, server, and/or computing device as described with reference to the previous FIGS. 1-5 to implement optical central venous pressure measurement. In embodiments, computing system 600 can be implemented as one or a combination of a wired and/or wireless wearable device, System-on-Chip (SoC), and/or as another type of device or portion thereof. Computing system 600 may also be associated with a user (e.g., a person) and/or an entity that operates the device such that a device describes logical devices that include users, software, firmware, and/or a combination of devices.

Computing system 600 includes communication devices 602 that enable wired and/or wireless communication of device data 604 (e.g., received data, data that is being received, data scheduled for broadcast, data packets of the data, etc.). Device data 604 or other device content can include configuration settings of the device, media content stored on the device, and/or information associated with a user of the device. Media content stored on computing system 600 can include any type of audio, video, and/or image data, including complex or detailed results of optical CVP-measuring acts. Computing system 600 includes one or more data inputs 606 via which any type of data, media content, and/or inputs can be received, such as human utterances, user-selectable inputs (explicit or implicit), messages, music, television media content, recorded video content, and any other type of audio, video, and/or image data received from any content and/or data source.

Computing system 600 also includes communication interfaces 608, which can be implemented as any one or more of a serial and/or parallel interface, a wireless interface, any type of network interface, a modem, and as any other type of communication interface. Communication interfaces 608 provide a connection and/or communication links between computing system 600 and a communication network by which other electronic, computing, and communication devices communicate data with computing system 600.

Computing system 600 includes one or more processors 610 (e.g., any of microprocessors, controllers, and the like), which process various computer-executable instructions to control the operation of computing system 600 and to enable techniques for, or in which can be embodied, optical central venous pressure measurement. Alternatively or in addition, computing system 600 can be implemented with any one or combination of hardware, firmware, or fixed logic circuitry that is implemented in connection with processing and control circuits which are generally identified at 612. Although not shown, computing system 600 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Computing system 600 also includes computer-readable media 614, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Computing system 600 can also include a mass storage media device 616.

Computer-readable media 614 provides data storage mechanisms to store device data 604, as well as various device applications 618 and any other types of information and/or data related to operational aspects of computing system 600. For example, an operating system 620 can be maintained as a computer application with computer-readable media 614 and executed on processors 610. Device applications 618 may include a device manager, such as any form of a control application, software application, signal-processing and control module, code that is native to a particular device, a hardware abstraction layer for a particular device, and so on.

Device applications 618 also include any system components, engines, or managers to implement the techniques. In this example, device applications 618 include a CVP-measurement manager 312.

CONCLUSION

Although embodiments of techniques using, and apparatuses enabling, optical central venous pressure measurement have been described in language specific to features and/or methods, it is to be understood that the subject of the appended claims is not necessarily limited to the specific features or methods described. Rather, the specific features and methods are disclosed as example implementations of these techniques.

What is claimed is:

1. A method for outputting a central venous pressure (CVP) of a person computed by at least one computing device, the method comprising:
   generating, by the at least one computing device and using a camera associated with the at least one computing device, a video of the person raising their hands;
   generating, by the at least one computing device, a reconstructed video in which motion that results from at least one of veins collapsing in the person's arms or a change in pulse is amplified based on detection of the collapsing of veins in the person's arms or the change in the person's pulse at different spatial frequency bands by processing the video according to one or more video motion amplification techniques;
   measuring, by the at least one computing device, an angle and height of the raised hands, relative to the person's heart, in the reconstructed video at a time that corresponds to the collapsing of the veins or the change in pulse;
   computing, by the at least one computing device, the CVP of the person based on the measured angle and height of the raised hands; and
   outputting, by the at least one computing device, digital content indicative of the computed CVP.

2. The method as described in claim 1, wherein:
   the motion that results from the at least one of the collapsing of veins in the person's arms or the change in pulse in the video of the person raising their hands is visually imperceptible to an unaided human eye; and
   the motion that results from the at least one of the collapsing of veins in the person's arms or the change in pulse in the reconstructed video is visually perceptible by the unaided human eye.

3. The method as described in claim 1, wherein processing the video according to one or more video motion amplification techniques to generate the reconstructed video includes, by the at least one computing device:
   spatially decomposing the captured video into different spatial frequency bands;
   applying temporal filters to filter for the pulsatile motion at the different spatial frequency bands; and
   visually amplifying the motion that results from the at least one of the collapsing of veins in the person's arms or the change in pulse based in part on the different spatial frequency bands in which the motion is observed.

4. The method as described in claim 1, further comprising generating a user interface to present the digital content indicative of the computed CVP on a display device.

5. The method as described in claim 1, further comprising:
comparing the CVP to one or more previously computed CVPs, the one or more previously computed CVPs having each been determined by performing the generating, the measuring, and the computing for a respective previously generated video; and
determining a trend in cardiovascular health of the person based on results of comparing the CVP to the one or more previously-determined CVPs.

6. The method as described in claim 1, further comprising:
generating, by the at least one computing device and using the camera associated with the at least one computing device, another video that includes the person's neck;
generating, by the at least one computing device, another reconstructed video in which pulsatile motion of the person's venous system that occurs in the person's neck is amplified based on detection of the pulsatile motion at different spatial frequency bands by processing the other video according to the one or more video motion amplification techniques;
calculating, by the at least one computing device, a distance between a detected peak of the amplified pulsatile motion and a selected anatomical feature of the person; and
computing, by the at least one computing device, another CVP of the person based on the calculated distance for the amplified pulsatile motion.

7. The method as described in claim 6, wherein the selected anatomical feature corresponds to a mandibular angle of the person or an ear lobe of the person.

8. The method as described in claim 6, further comprising determining the selected anatomical feature relative to which to measure the distance based in part on the person's anatomical features that remain visible in the reconstructed video when the distance is calculated.

9. The method as described in claim 6, further comprising:
analyzing the reconstructed video by the at least one computing device to determine a breathing rate of the person; and
performing the calculating during respiratory pauses of the determined breathing rate.

10. A device comprising:
a video camera to capture video of a person raising their hands;
a display device to display a reconstructed video of the person raising their hands; and
a processing system to implement a central venous pressure (CVP) measurement manager configured to:
generate the reconstructed video in which motion that results from at least one of veins collapsing in the person's arms or a change in pulse is amplified based on detection of the collapsing of veins in the person's arms or the change in the person's pulse at different spatial frequency bands by processing the video according to one or more video motion amplification techniques;
measure an angle and height of the raised hands, relative to the person's heart, in the reconstructed video at a time that corresponds to the collapsing of veins or the change in pulse;
compute CVP measurements for the person based on the measured angle and height of the raised hands; and
present digital content indicative of the CVP measurements.

11. The device as described in claim 10, further comprising storage media configured to store CVP measurements that are determined at different times for access by the CVP-measurement manager to determine a trend in cardiovascular health of the person based on a comparison of the stored CVP measurements.

12. The device as described in claim 10, wherein:
the device is configured as a smartphone; and
an application embodied on the smartphone enables a user to initiate the CVP-measurement manager to determine the CVP measurements of the person.

13. The device as described in claim 10, further comprising one or more hyperspectral cameras, the CVP-measurement manager being further configured to locate the collapsing veins of the person using at least one of images or videos captured with the one or more hyperspectral cameras, and process the captured video by applying the one or more video motion amplification techniques to the portions of the video that correspond to the located veins.

14. The device as described in claim 10, wherein:
the motion that results from the at least one of the collapsing of veins in the person's arms or the change in pulse is visually imperceptible to an unaided human eye; and
the motion that results from the at least one of the collapsing of veins in the person's arms or the change in pulse is visually perceptible by the unaided human eye in the reconstructed video.

15. The device as described in claim 14, further comprising at least one of:
one or more lasers employed by the CVP-measurement manager to detect the motions that result from the at least one of the collapsing of veins in the person's arms or the change in pulse; or
one or more light emitting devices that emit structured light and are employed by the CVP-measurement manager to detect the motions that result from the at least one of the collapsing of veins in the person's arms or the change in pulse.

16. The device as described in claim 10, wherein
the video camera captures another video that includes the person's neck; and
the CVP-measurement manager is further configured to:
generate another reconstructed video in which pulsatile motions of the person's venous system that occur in the person's neck are amplified based on detection of the pulsatile motions at different spatial frequency bands by processing the other video according to the one or more video motion amplification techniques;
calculate distances in frames of the other reconstructed video between detected peaks of the amplified pulsatile motions and a selected anatomical feature of the person;
compute additional CVP measurements for the person based on the calculated distances; and
present digital content indicative of the additional CVP measurements.

17. The device as described in claim 16, wherein the CVP-measurement manager is further configured to:
analyze the other reconstructed video to determine a breathing rate of the person; and
calculate the distances between the peaks of the visually-amplified pulsatile motions and the anatomical feature of the person during respiratory pauses in the determined breathing rate.

18. A computer-implemented method comprising:
generating video of a person raising their hands two or more times;

determining a first central venous pressure (CVP) of the person at a first time that corresponds to a first raising of the person's hands based, in part, on measuring an angle and height of the person's raised hands, relative to the person's heart, that corresponds to at least one of a collapsing of the person's veins or a change in the person's pulse, the angle and height measured in a frame of a first reconstructed video associated with the first time and in which the motion that results from the at least one of the collapsing of veins in the person's arms or the change in pulse is amplified based on detection of the collapsing of veins in the person's arms or the change in the person's pulse at different spatial frequency bands by processing the video according to one or more video motion amplification techniques;

determining a second CVP of the person at a second time that corresponds to a second raising of the person's hands based, in part, on measuring an angle and height of the person's raised hands, relative to the person's heart, that corresponds to at least one of a second collapsing of the person's veins or a second change in the person's pulse, the angle and height measured in a frame of a second reconstructed video associated with the second time and in which the motion that results from the at least one of the collapsing of veins in the person's arms or the change in pulse is amplified based on detection of the collapsing of veins in the person's arms or the change in the person's pulse at different spatial frequency bands by processing the video according to the one or more video motion amplification techniques; and determining a trend in the cardiovascular health of the person based on a comparison of the first CVP determined at the first time and the second CVP determined at the second time.

19. The computer-implemented method as described in claim 18, further comprising communicating the first CVP and the second CVP to a remote computing device for storage with medical records associated with the person.

20. The computer-implemented method as described in claim 18, further comprising accessing the first CVP and the second CVP from medical records stored in association with the person to determine the trend in the cardiovascular health of the person.

\* \* \* \* \*